United States Patent [19]
Reno

[11] Patent Number: 4,751,751
[45] Date of Patent: Jun. 21, 1988

[54] DISPOSABLE URINATING FUNNEL FOR FEMALES

[76] Inventor: Richard C. Reno, 21401 Hoover Rd., Warren, Mich. 48089

[21] Appl. No.: 887,734

[22] Filed: Jul. 21, 1986

[51] Int. Cl.$^4$ .............................................. E03P 13/00
[52] U.S. Cl. ..................................... 4/144.4; 141/337
[58] Field of Search ............................. 4/144.1–144.4, 4/114.1; 604/347, 329; 141/337

[56] References Cited

U.S. PATENT DOCUMENTS

| | | | |
|---|---|---|---|
| 2,100,888 | 11/1937 | Vine | 141/337 |
| 2,158,688 | 5/1939 | Brooks | 141/337 |
| 3,746,240 | 7/1973 | Flynn | 4/144.2 |
| 3,844,337 | 10/1974 | Bessett et al. | 141/337 |
| 3,964,111 | 6/1976 | Packer | 4/144.4 |
| 4,023,216 | 5/1977 | Li | 4/144.3 |
| 4,108,222 | 8/1978 | Kaufman | 141/337 |

Primary Examiner—Henry J. Recla
Assistant Examiner—L. J. Peters
Attorney, Agent, or Firm—Cullen, Sloman, Cantor, Grauer, Scott and Rutherford

[57] ABSTRACT

A disposable urinating funnel for females comprises a thin, paper-like sheet which is folded in half to form two overlapping sections whose free edges are connected together and are tapered toward the fold line to form a funnel-like shape. The upper edges of the funnel-shape are curved to cover a female vaginal area, and the opposite, bottom edges form a spout-like portion. Score lines are formed midway between the fold line and connected side edges in each of the sections and extend upwardly from the bottom of the spout-forming portion toward the upper end of the funnel-like shape. Manually squeezing the fold line and connected side edges toward each other causes the otherwise flat funnel-like shape to open, by bowing the sections apart along the score lines. In addition, the tapered, connected-together edges are cut along a shallow curve which permits the funnel to be used with the fold line forwardly or rearwardly for selectively directing the flow of liquid through it.

10 Claims, 1 Drawing Sheet

DISPOSABLE URINATING FUNNEL FOR FEMALES

BACKGROUND OF INVENTION

For purposes of medical treatment and medical testing, it is frequently necessary to collect urine specimens from female patients. The specimens are normally collected in relatively small-size bottles so that it is awkward and difficult for a patient to direct her urine into a bottle for collection.

Further, there are other situations where it is necessary or desirable for a female to be able to urinate while standing up or otherwise directing the flow of urine from her body to some particular location which is awkward to accomplish under normal conditions. Thus, while attempts have been made in the past to provide urine-collecting or directing devices for female use, in general these have been relatively expensive, bulky, and awkward to use.

Therefore, for medical as well as other purposes, there has been a need for a funnel-like device useful for directing the flow of urine from female to a particular location, but which device is compact for easy carrying and storage, is extremely inexpensive so that it is disposable after a single use, and, in addition, is easy and convenient to use.

SUMMARY OF INVENTION

The invention herein relates to a disposable, funnel-like device useful for collecting and directing the flow of urine from a female body, which device is made of a flat sheet of paper-like material which is folded in half to form two overlapping sections whose free edges are connected together and tapered into a funnel-like shape. The upper edges of the sections are curved to envelop the exterior of the female vaginal area, and the lower portion of the funnel-like device is formed in a spout-like shape. The invention contemplates a one-hand operation accomplished by manually squeezing the fold line portion of the funnel-like device toward the connected edges, using the forefinger and thumb of the user's hand. This pressure causes the sections to bow apart for opening of the funnel for use.

In order to open the funnel symmetrically under the manual squeezing pressure, score lines are provided approximately midway between the fold line and joined side edges. These lines extend upwardly from the bottom of the spout portion, part way towards the upper, open mouth of the funnel and form lines for bending or bowing the sections. The funnel-like device is formed of a relatively thin, stiff but somewhat flexible, paper-like material which is sufficiently waterproof or water-resistant for the purpose intended. Thus, the device may normally be stored flat, and a number of them may be easily kept together in a stack which may be provided in a bathroom or laboratory area or within a woman's pocketbook for use as needed.

It is contemplated to curve the overlapped, connected side edges of the sections. This permits the funnel-like device to be reversed, with either the curved edges or the fold line being arranged forwardly in use. Thus, the user can selectively direct the flow of urine downwardly or, alternatively, relatively forwardly of her body as is more convenient.

One object of this invention is to provide an extremely inexpensive, throw-away funnel for use in medical laboratories, hospitals or private homes which can be used once for collecting urine specimens and then discarded. The funnel is so formed as to make it easy to use with one hand which opens it and holds it in position during use for directing urine to the desired bottle or other location.

Another object of this invention is to provide a funnel which is paper-like in its construction so that it can be stacked, that is, it can be handled in the same way that flat sheets of paper or paper towels are handled to simplify storage, use and availability and to permit immediate disposal upon use.

These and other objects and advantages of this invention will become apparent upon reading the following description, of which the attached drawings form a part.

DETAILED DESCRIPTION

Figure 1:
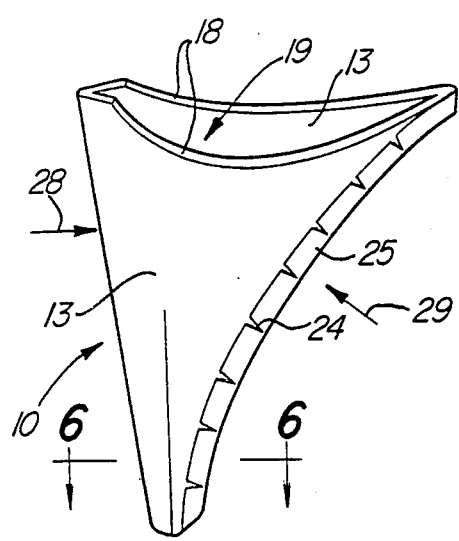
FIG. 1 is a perspective view of the funnel in open position.
Figure 3:
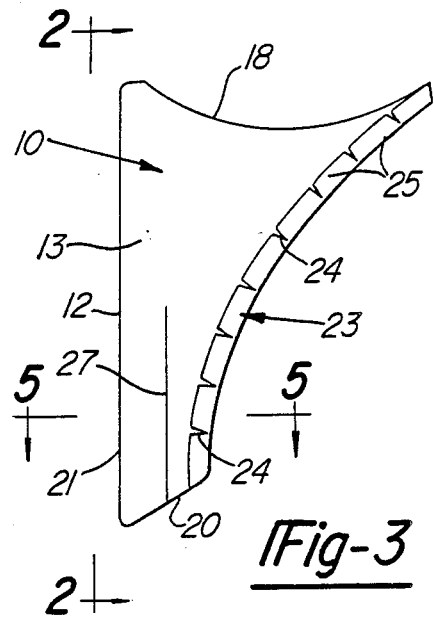
FIG. 3 is a front elevational view of the funnel in its flat condition.
Figure 2:
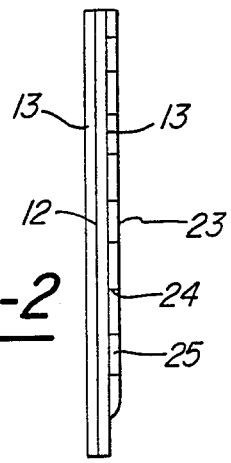
FIG. 2 is a side elevational view taken in the direction of arrows 2—2 of FIG. 3.
Figure 5:
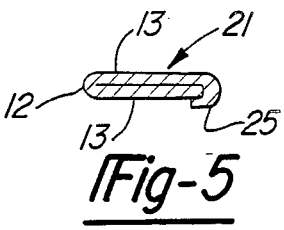
FIG. 5 is a fragmentary, cross-sectional view taken in the direction of arrows 5—5 of FIG. 3, showing the spout portion flat.

Referring to the drawings, the funnel 10 is formed of a flat sheet 11 of a paper-like material which is thin, relatively stiff like heavy paper, but somewhat flexible. The paper-like material may be made of either conventional paper which is sufficiently treated so as to be waterproof or water-resistant for a short time or of plastic sheet material having similar characteristics. Paper is preferred as it is more disposable and biodegradable than plastic.

Figure 4:
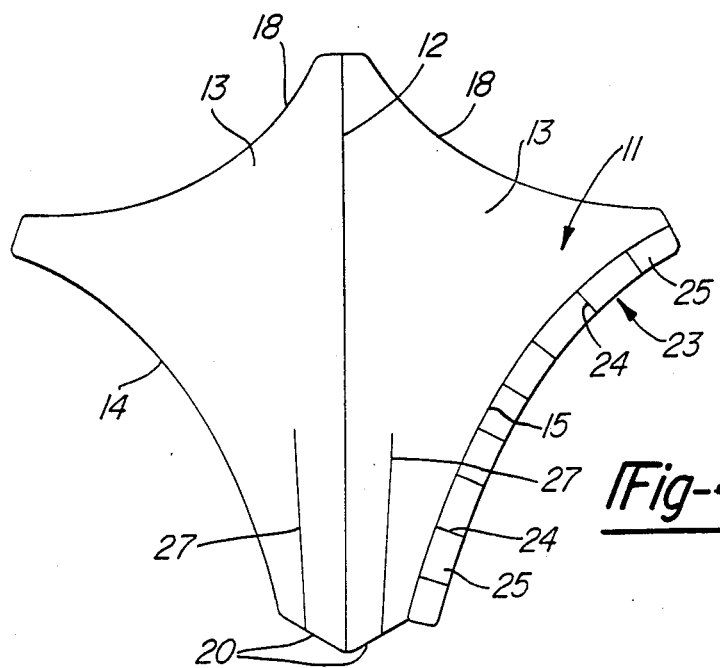
FIG. 4 is an elevational view showing the funnel sheet open and flat, before folding into the funnel shape.

The sheet is provided with a fold line 12 (see FIG. 4) which divides it into two substantially identical sections 13 having opposed side edges 14 and 15. The side edges are tapered or angled in the downward direction and preferably are cut along a shallow curve to form a funnel-like shape. The upper edges 18 of the funnel are curved to fit over or envelop the vaginal area of a female. This provides a mouth or funnel inlet 19 which can be easily manually positioned over the vaginal area whether the user is seated or standing.

The bottom edges of the funnel shape are formed as upwardly angled lower edges 20 which, together with the lower curved portions of the side edges and the fold line, form a lower spout portion 21.

The side edges 14 and 15 are connected together. In the embodiment shown in the drawings, the connection is provided by a narrow, integral strip 23 formed along the curved side edge 15. The strip has spaced apart slits 24 between which tabs 25 are formed. The tabs can be bent over, so as to overlap, the edge portion adjacent the tapered side edge 14 where they can be secured adhesively using any suitable, commercially available adhesive. It is also possible to adhesively secure the adjacent side edge portions directly together without the additional strip 23 and its tabs.

At least one score line 27 is formed in each of the sections roughly midway between the fold line 12 and the respective edges 14 and 15. The fold lines extend from the bottom of the funnel toward the upper mouth portion of the funnel. As can be seen in the drawings, the score lines are preferably about one-half the height of the funnel sections, although the height of the score lines may be varied depending upon the stiffness of the paper to enhance bending of the sections.

Figure 6:
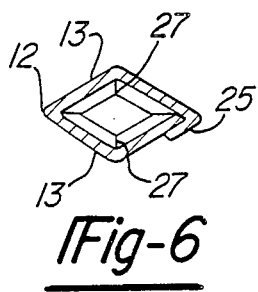
FIG. 6 is a fragmentary, cross-sectional view taken in the direction of arrows 6—6 of FIG. 1 showing the spout portion open.

In operation, the assembled funnel, that is, the funnel with the sections folded into overlapping position and with their edges joined together is stored flat until needed. When needed, the user positions the funnel adjacent her body and by squeezing the fold line and connected edges together, between her thumb and forefinger, as indicated by the arrows 28 and 29 in FIG. 1, both holds and opens the funnel into its use position. The score lines 27 ensure that the sections bow apart symmetrically, particularly at the lower spout portion of the funnel, as illustrated in FIG. 6. Upon completion of its use, the squeezing pressure is relieved, so that the funnel flattens out, and the funnel can be thrown away.

Because of the curved shape of the adjacent edges, opposing the straight line of the fold line, the funnel may be used reversely for directing the flow of liquid either downwardly or forwardly. Thus, is the position illustrated in FIG. 1, the flow of liquid would be directed downwardly. However, by placing the curved edge forwardly of the user, the urine may be directed forwardly. Thus, the user may selectively position the funnel as is more convenient for her use.

Having fully described an operative embodiment of this invention, I now claim:

1. A disposable urinating funnel for females, comprising:
   a thin, flat sheet of relatively stiff, somewhat flexible, paper-like material folded in half into two overlapping, substantially identical, normally flat sections which are joined together along a normally, substantially upright fold line and having overlapping free side edges opposite the fold line and upper edges extending between the fold line and the side edges;
   the sides being connected together and the upper edges being free of attachment;
   said side edges being curved outwardly away from said fold line forming a wide upper body portion which tapers downwardly into a narrow bottom opening spout;
   said upper edges being shaped to generally cover a female vagina area;
   said sections having at least one score line formed in each section extending from the bottom edge of the spout, generally parallel with the fold line for a distance upwardly part-way toward the upper edges;
   said funnel being operable with one handed application of pressure at said fold line and said side edges adjacent the bottom of said sections with said score line creasing at the bottom spout-forming portions of said sections to form a generally rectangular spout portion and said upper sections respectively bowing outwardly without creasing to form an opening that closely conforms to the female anatomy;
   wherein the pressure of squeezing said fold line and said side edges adjacent the bottom of said sections causes such sections to bow apart sufficiently to open the funnel for use.

2. A disposable urinating funnel as defined in claim 1, wherein said side edges are formed as a shallow curve extending from the upper edges toward the bottom of the sections such that the funnel is reversable with the said spout respectively angled forwardly or rearwardly with respect to said female.

3. The disposable urinating funnel of claim 1 wherein said upper edges are concavely curved from adjacent said fold line to said side edges such that upon application of pressure at said fold line and side edges said sections bow apart sufficiently to open the funnel for use and to envelope the vaginal area.

4. A disposable urinating funnel as defined in claim 1, and said side edges being connected together by a narrow edge strip integral with one of the side edges, with the strip being folded around, overlapping and fastened to the other side edge to form a folded, closed seam.

5. A disposable urinating funnel as defined in claim 1, and including the side edge taper being formed as a shallow curve and extending from the upper edge toward the bottom of the funnel;
   and the side edges being connected together by a narrow edge strip formed integral with one of the side edges and being folded over and overlapping and being fastened to the other side edge to form a folded seam.

6. A disposable urinating funnel as defined in claim 1, and including the bottom edge of the spout being cut at an angle which extends upwardly away from said fold line toward the side edges.

7. A disposable urinating funnel for females, comprising:
   a thin, flat sheet of relatively stiff, somewhat flexible paper-like material folded in half into two overlapping, substantially identical, normally flat sections which are joined together along a normally, substantially upright fold line and having overlapping free side edges opposite the fold line and upper edges extending between the fold line and the side edges;
   said sides being connected together and said upper edges being free of attachment;
   said side edges being generally tapered downwardly from the upper edges toward the bottom of the sections to form a narrow, bottom opening spout, said taper being formed as a shallow curve extending from the upper edges toward the bottom of the sections such that the funnel is reversable with said spout respectively angled forwardly or rearwardly with respect to said female;
   said upper edges being shaped to generally cover a female vaginal area;
   said sections having at least one score line formed in each section and extending from the bottom edge of the spout generally parallel with the fold line, for a distance upwardly part-way toward the upper edges said score line being limited in length such that upon application of pressure at said side edges and said fold lines, said score lines are creased along substantially their entire length to form said spout while said upper portions of said sections are bowed apart between the fold line and the side edges to form an opening at said upper edges which closely conforms to the female anatomy, said funnel being operable with one-handed application of pressure at said fold line and said side edges adjacent the bottom spout-forming portions of said sections to form a generally rectangular spout portion and said upper sections respectively bowing outwardly without creasing to form an opening that closedly conforms to the female anatomy.

8. A disposable urinating funnel as defined in claim 7, wherein said side edges are connected together by a narrow edge strip integral with one of the side edges, said strip being folded around, overlapping and fastened to the other side edge to form a folded, closed seam.

9. The disposable urinating funnel as defined in claim 7, wherein the bottom edge of the spout is cut at an angle which extends upwardly away from said fold line toward said side edges.

10. The disposable urinating funnel of claim 7, wherein said upper edges are concavely curved from adjacent said fold line to said side edges such that upon application of pressure at said fold line and side edges said sections bow apart sufficiently to open the funnel for use and to envelope the vaginal area.

* * * * *